United States Patent [19]

Degen et al.

[11] Patent Number: 4,961,861
[45] Date of Patent: Oct. 9, 1990

[54] PROCESS FOR WORKING UP HYDROLYSIS RESIDUES FROM THE SYNTHESIS OF ORGANOCHLOROSILANES

[75] Inventors: Bruno Degen, Much; Kurt Feldner, Leverkusen, both of Fed. Rep. of Germany

[73] Assignee: Bayer Aktiengesellschaft, Leverkusen, Fed. Rep. of Germany

[21] Appl. No.: 394,606

[22] Filed: Aug. 16, 1989

[30] Foreign Application Priority Data

Sep. 10, 1988 [DE] Fed. Rep. of Germany ....... 3829581

[51] Int. Cl.$^5$ ............................................. B01D 21/00
[52] U.S. Cl. .................................. 210/717; 210/721; 210/758; 556/477
[58] Field of Search ............... 210/708, 710, 717, 721, 210/758; 252/321, 351; 556/472, 477

[56] References Cited

U.S. PATENT DOCUMENTS

| 2,380,995 | 8/1945 | Rochow ............................. 556/472 |
| 4,221,691 | 7/1975 | Danielson et al. ........... 260/33.6 SB |
| 4,244,818 | 1/1981 | Abson ................................. 210/721 |
| 4,408,030 | 10/1983 | Marko ................................... 528/10 |
| 4,422,880 | 12/1983 | Wason et al. ....................... 106/466 |
| 4,758,352 | 7/1988 | Feldner et al. ...................... 210/719 |

FOREIGN PATENT DOCUMENTS

| 0089783 | 9/1983 | European Pat. Off. ............. 528/10 |
| 0210418 | 2/1987 | European Pat. Off. ............ 210/719 |
| 2362494 | 7/1975 | Fed. Rep. of Germany . |
| 3005754 | 8/1980 | Fed. Rep. of Germany ..... 260/33.6 SB |
| 3523543 | 1/1987 | Fed. Rep. of Germany ...... 210/719 |
| 2079698 | 10/1971 | France ................................. 210/778 |

Primary Examiner—Peter Hruskoci
Assistant Examiner—Krisanne Shideler
Attorney, Agent, or Firm—Sprung Horn Kramer & Woods

[57] ABSTRACT

A process is disclosed for working up the high-boiling, solids-containing residues obtained in the synthesis of organochlorosilanes which are hydrolyzed and then optionally oxidized, with oxygen-containing gases, comprising adding during hydrolysis and/or oxidation a surface-active substance which hydrophilicizes the surface of the solids.

5 Claims, 1 Drawing Sheet

PROCESS FOR WORKING UP HYDROLYSIS RESIDUES FROM THE SYNTHESIS OF ORGANOCHLOROSILANES

BACKGROUND OF THE INVENTION

1. Field of the Invention

This invention relates to a process for working up hydrolysis residues obtained in the hydrolysis of solids-containing polysilane sludges from the synthesis of organochlorosilanes by the direct process. More particularly, the invention relates to the working up of hydrolysis residues from the synthesis of methylchlorosilanes.

2. Background Information

Organochlorosilanes and, in particular, methylchlorosilanes are used as starting materials for the production of silicones which are widely used, for example, as rubbers, jointing compounds, oils, structural sealants, etc. Dimethyldichlorosilane is required in particular for the production of methylchlorosilanes, being obtained in high yields when the direct reaction of silicon with methylene chloride is catalyzed by copper or copper compounds. The process is described in principle in U.S. Pat. No. 2,380,995. The industrial production of methylchlorosilanes by this process is carried out worldwide, the reaction normally being carried out in continuous fluidized-bed reactors.

Where the direct process is carried out in fluidized-bed reactors, the very fine fractions of silicon, catalyst and unreacted contact material are continuously discharged together with the reaction product, the crude silane mixture, and unreacted methyl chloride.

These dust-like fines are often collected together with the highest-boiling reaction products ($Bp_{760} > 160°$ C.) in a so-called sludge vessel followed by a washing tower. The temperature of the vessel, which is under the usual excess pressure of 1.5-10 bar, is generally adjusted so that the mixture of solids and condensed fractions is kept sufficiently thinly liquid to facilitate discharge from the vessel.

According to DE-PS 2 362 494, the contents of the vessel may be expanded in a stirred container preferably kept at normal pressure and the distillable components are removed from the mixture by heating. The contents of the vessel are then generally hydrolyzed.

The hydrolysis itself may be carried out in a downpipe, as described in DE-PS 2 362 494. The disadvantage is that, in view of the short contact times, hydrolysis is often incomplete and large quantities of water are consumed.

U.S. Pat. No. 4,221,691 describes a hydrolysis process in which the unpleasant property that the hydrolyzates have of sticking is prevented by the addition of mineral oil. However, since the hydrolyzates are regarded as worthless and are dumped, the additional organic pollution they cause is a disadvantage.

It is known from U.S. Pat. No. 4,408,030 that the problems of sticking can also be overcome by maintaining a minimum chlorine content, although technically this is difficult to do.

In all the processes mentioned above, a hydrochloric acid suspension is formed in which the more or less solid hydrolyzate is regarded as worthless and has to be dumped. However, the hydrolyzates are not without problems because they generally contain 2 to 10% predominantly metallic copper which can be partly eluted from the dumped hydrolyzate, thus endangering the ground water. In addition, most of the hydrolyzates obtained are vulnerable to oxidation and, in some case, even show a tendency to ignite spontaneously so that they cannot be safely dumped.

Now, U.S. Pat. No. 4,758,352 describes a process in which the hydrolysis is carried out in water or a heavily diluted hydrochloric acid in a stirred container which is equipped with a high-speed disk stirrer, but not with baffles so that a vortex into which the material to be hydrolyzed is introduced can form. The preferred temperature is between 60° and 90° C. A suspension of finely divided solid hydrolyzates, in which more than 90% of the solid particles are smaller than 5 mm in diameter, is thus obtained.

The suspensions thus obtained are then oxidized with oxygen-containing gases which, according to the invention cited above, is preferably done with technically pure oxygen under a pressure above atmospheric pressure.

On completion of oxidation, solids and copper-containing liquid are separated from one another.

The process according to U.S. Pat. No. 4,758,352 gives a disposable, compact, non-gasing solid with no elutable heavy metals which is thermally inert in the context of the invention and may thus be safely dumped.

SUMMARY OF THE INVENTION

Now, the present invention relates to a process for working up high-boiling, solids-containing residues obtained in the synthesis of organochlorosilanes which are hydrolyzed and then oxidized, characterized in that a surface-active substance which hydrophilicizes the surface of the solids is added during hydrolysis and/or oxidation.

The addition of a surface-active substance in accordance with the invention is not confined to the combination of hydrolysis and oxidation and may also be applied where hydrolysis is carried out without subsequent oxidation. In general, the better wetting reduces the tendency of the hydrolyzate to stick, thus reducing contamination of the product-carrying parts of the plant.

Hydrolysis preferably comprises adding the surface-active substance to the water or the heavily diluted hydrochloric acid, which is fed to the stirred container comprising a high-speed disk stirrer for hydrolyzing the high-boiling solids-containing residue from the synthesis of organochlorosilanes, and thus hydrophilicizing the surface.

Oxidation preferably comprises adding the surface-active substance hydrophilicizing the surface to the suspension to be oxidized during filling of the oxidation reactor. It is also possible to add part of the surface-active substance during hydrolysis and another part during oxidation.

The surprising advantage of the working-up process according to the invention is that it provides for better wetting of the high-boiling, solids-containing residue to be hydrolyzed and hence for more effective hydrolysis and that oxidation, which according to the invention is preferably carried out by exposing the suspension obtained during hydrolysis to technically pure oxygen under a pressure above atmospheric pressure at temperatures of $80° \pm 10°$ C., is not accompanied by any flotation and foaming effects, which could adversely affect the conduct of the reaction.

The substances which influence the surface properties of the hydrolyzate in accordance with the invention are purely inorganic by nature and form a deposit in the mineral acid medium, which is adsorbed onto the surface of the hydrolyzate and thus creates the hydrophilic character.

Suitable substances are either alkaline silicate solutions, such as, for example, waterglass solution, or silica sols. Where the substances mentioned are added to the hydrolyzate suspension or to the hydrolysis water, $SiO_2$ is precipitated under the effect of the hydrochloric acid already present or the hydrochloric acid formed during hydrolysis. The finely divided deposit is absorbed onto the surface of the hydrolyzate, which is then hydrophilicized by virtue of the hydrophilic character of the deposit.

The quantity of surface-active or hydrophilic substance required depends on the quantity of solids present in the suspension and their fineness.

In most cases, suspensions of 20 to 30% by weight solid hydrolyzate, determined as moist filter cake, are required for hydrolysis. Experience has shown that between 100 and 5000 ppm, expressed as parts by weight of the active substance based on the suspension as a whole, have to be used for suspensions such as these. Additions of 200 to 3000 ppm active substance, based on the suspension as a whole, are preferred.

The inorganic substances used in accordance with the invention have the advantage that their use does not add to the organic pollution of the wastewater.

BRIEF DESCRIPTION OF THE DRAWING

The preferred embodiment of the process according to the invention is described in detail in the following with reference to the accompanying drawing and the Examples which are purely illustrative and are not intended to limit the invention in any way.

DETAILED DESCRIPTION OF THE INVENTION

Figure 1:
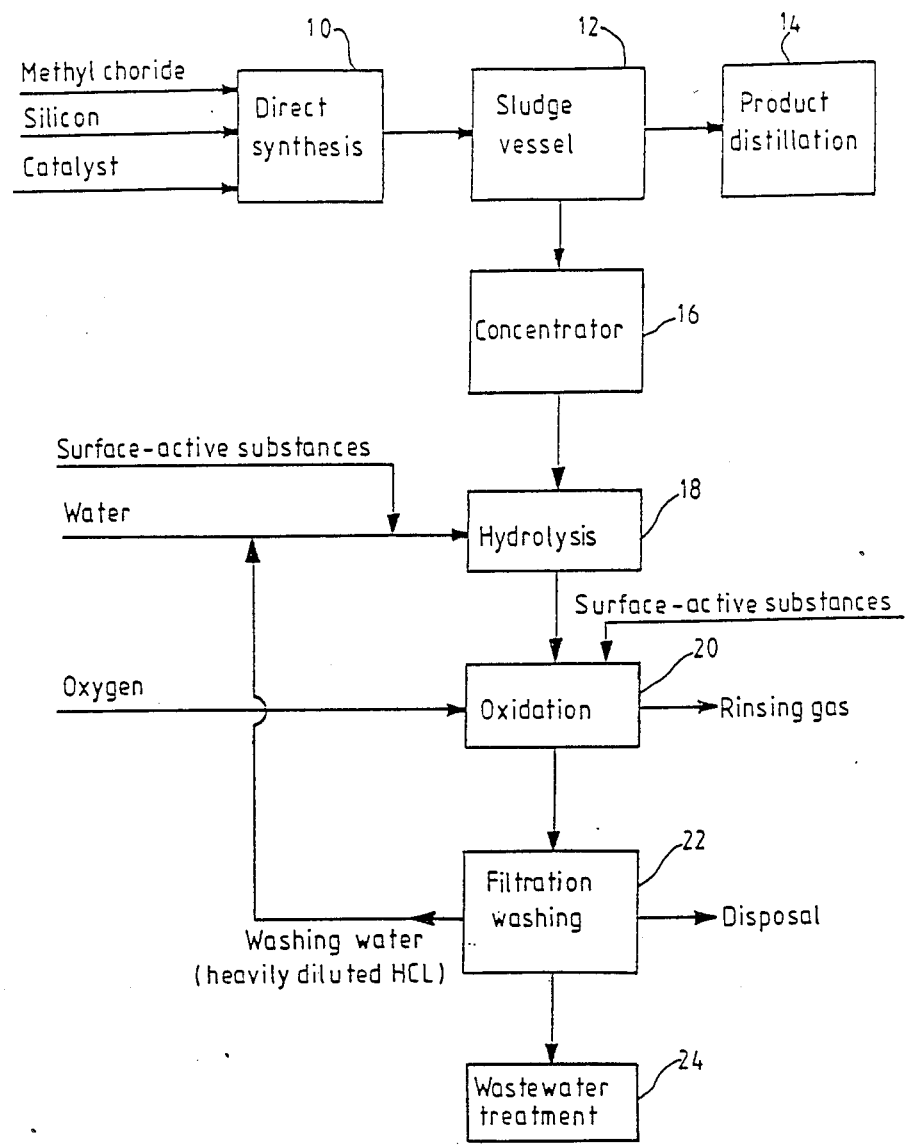
FIG. 1 schematically depicts the inventive process.

FIG. 1 shows the standard procedure. Gaseous reaction products, unreacted methyl chloride and fines enter the sludge vessel 12 from the "direct synthesis reactors" 10. The non-volatile constituents are collected in the sludge vessel 12. The volatile constituents leave the vessel 12 for the product distillation stage 14. By means of a cycle valve, the non-volatile contents are expanded and introduced into a concentrator 16 to recover compounds which are volatile at atmosheric pressure.

Hydrolysis is carried out with water or dilute HCl in a stirrer-equipped reaction vessel 18.

Now, surface-active substances may be added in accordance with the invention to the water required for hydrolysis through the water inlet or, if desired, not until the next step, i.e., during filling of the oxidation reactor 20, in which the liquid is exposed to the gas containing the elemental oxygen; partial quantities may optionally be added at both places. After oxidation, the solid is separated from the aqueous liquid in a suitable filtration unit 22, the aqueous liquid is fed to a suitable wastewater treatment plant 24 and the solid is washed and then dumped. The washing water may optionally be reused for hydrolysis.

The invention will now be described with reference to the following non-limiting Example.

EXAMPLE

The Example shows the change in the foaming and wetting behavior of a hydrolysis suspension brought about by the addition of silica sol. The experiments were carried out in a gassing apparatus with three baffles and a gassing stirrer.

Gassing Conditions

Gassing stirrer diameter = 4.6 cm
Stirring speed: 1585±30 r.p.m.
Vessel diameter: 15 cm
Vessel height: 60 cm
Filling level: approx. 17.5 cm The suspension (3 kg) had a concentration of 20% by weight moist solids.

The anionic BAYER silica sols 100/30%, 200/30% and 300/30% (products of Bayer AG, Leverkusen), were used.

| Quantity added: 3 ml | Foam height during gassing | Settling behavior of solids after gassing |
|---|---|---|
| Silica sol 100/30% | 3 cm | Foam collapses immediately, solids completely wetted |
| Silica sol 200/30% | 3 cm | Foam collapses immediately, solids completely wetted, approx. 50% sediment |
| Silica sol 300/30% | 3 cm | Foam collapses immediately, solids sediment |
| Comparison test with no addition | 35 cm | Foam remains stable approx. 20% solids float |

It will be appreciated that the instant specification and claims are set forth by way of illustration and not limitation, and that various modifications and changes may be made without departing from the spirit and scope of the present invention.

What is claimed is:

1. A process for hydrolyzing and optionally oxidizing high-boiling, solids-containing residues obtained in the synthesis of organochlorosilanes which are hydrolyzed and then optionally oxidized with oxygen-containing gases, comprising adding during hydrolysis and/or oxidation a surface-active substance which hydrophilicizes the surface of the solids, wherein the surface-active substance is an inorganic deposit which is produced in solution and precipitates onto the surface of the solids.

2. A process as claimed in claim 1, wherein the inorganic deposit is $SiO_2$ produced from waterglass solution or silica sol.

3. A process as claimed in claim 1, wherein the surface-active substance is in an amount of from 100 ppm to 5,000 ppm, based on a suspension of hydrolyzed solids-containing residues in said hydrolysis.

4. A process as claimed in claim 3, wherein the amount is 200 to 3000 ppm.

5. A process as claimed in claim 1, wherein the surface-active substance is added to water entering the hydrolysis.

* * * * *

UNITED STATES PATENT AND TRADEMARK OFFICE
CERTIFICATE OF CORRECTION

PATENT NO. : 4,961,861

DATED : October 9, 1990

INVENTOR(S) : Degen et al.

It is certified that error appears in the above-identified patent and that said Letters Patent is hereby corrected as shown below:

Title Page     Foreign Application Priority Data: After " Sep. " delete " 10 " and substitute -- 01 --

Title Page     FOREIGN PATENT DOCUMENTS: Delete " 3005754 " and substitute -- 3005743 --

Title Page     ABSTRACT: Line 1 delete " is disclosed "

Signed and Sealed this

Eleventh Day of August, 1992

*Attest:*

DOUGLAS B. COMER

*Attesting Officer*     *Acting Commissioner of Patents and Trademarks*